US011826378B2

(12) United States Patent
Kroh et al.

(10) Patent No.: US 11,826,378 B2
(45) Date of Patent: Nov. 28, 2023

(54) USE OF SGLT-2 INHIBITORS FOR THE PREVENTION AND/OR TREATMENT OF CARDIAC DISEASES IN FELINES

(71) Applicant: Boehringer Ingelheim Vetmedica GmbH, Ingelheim am Rhein (DE)

(72) Inventors: Carla Kroh, Oestrich-Winkel (DE); Ingo Ulrich Lang, Ingelheim am Rhein (DE); Horst Rose, Burgdorf (DE); Franziska Roessner, Huettenstein (DE); Saskia Kley, Appenheim (DE)

(*) Notice: Subject to any disclaimer, the term of this patent is extended or adjusted under 35 U.S.C. 154(b) by 0 days.

(21) Appl. No.: 17/176,285

(22) Filed: Feb. 16, 2021

(65) Prior Publication Data
US 2021/0260090 A1    Aug. 26, 2021

(30) Foreign Application Priority Data
Feb. 17, 2020    (EP) .................... 20157761

(51) Int. Cl.
| A61K 31/7034 | (2006.01) |
|---|---|
| A61K 47/54 | (2017.01) |
| A61P 9/04 | (2006.01) |
| A61K 31/138 | (2006.01) |
| A61K 31/341 | (2006.01) |
| A61K 31/401 | (2006.01) |
| A61K 31/4184 | (2006.01) |
| A61K 31/4422 | (2006.01) |
| A61K 31/501 | (2006.01) |
| A61K 31/554 | (2006.01) |
| A61K 31/585 | (2006.01) |
| A61K 31/616 | (2006.01) |
| A61K 31/7042 | (2006.01) |
| A61K 31/7048 | (2006.01) |
| A61K 31/7056 | (2006.01) |
| A61K 31/727 | (2006.01) |

(52) U.S. Cl.
CPC ........ *A61K 31/7034* (2013.01); *A61K 31/138* (2013.01); *A61K 31/341* (2013.01); *A61K 31/401* (2013.01); *A61K 31/4184* (2013.01); *A61K 31/4422* (2013.01); *A61K 31/501* (2013.01); *A61K 31/554* (2013.01); *A61K 31/585* (2013.01); *A61K 31/616* (2013.01); *A61K 31/7042* (2013.01); *A61K 31/7048* (2013.01); *A61K 31/7056* (2013.01); *A61K 31/727* (2013.01); *A61K 47/545* (2017.08); *A61P 9/04* (2018.01)

(58) Field of Classification Search
CPC .. A61K 31/341; A61K 31/351; A61K 31/138; A61K 31/401; A61K 31/4184; A61K 31/4422; A61K 31/501; A61K 31/554; A61K 31/585; A61K 31/616; A61K 31/7034; A61K 31/7042; A61K 31/7048; A61K 31/7056; A61K 31/727; A61K 47/545; A61P 9/04; A61P 9/00
See application file for complete search history.

(56) References Cited

U.S. PATENT DOCUMENTS

| 2011/0046087 A1* | 2/2011 | Eickelmann ............. A61P 3/04 514/23 |
|---|---|---|
| 2011/0098240 A1 | 4/2011 | Dugi et al. |
| 2015/0164856 A1 | 6/2015 | Reiche et al. |
| 2016/0000816 A1 | 1/2016 | Broedl et al. |
| 2017/0266152 A1 | 9/2017 | Broedl et al. |
| 2019/0076395 A1 | 3/2019 | Lauring et al. |

FOREIGN PATENT DOCUMENTS

| JP | 2016540790 A | 12/2016 |
|---|---|---|
| WO | 2011153953 | 12/2011 |
| WO | 2015091313 A1 | 6/2015 |
| WO | 2017155841 A1 | 9/2017 |
| WO | 2021092341 A1 | 5/2021 |

OTHER PUBLICATIONS

Kaplan et al., Heart Failure Reviews, 2018, 23, p. 419-437. (Year: 2018).*
Nair et al., Drug Dev. Res., 2018, 18(79), p. 373-382. (Year: 2018).*
M.Hoenig et al.: "Effects of the sodium-glucose cotransporter 2 (SGLT2) inhibitor velagliflozin, a new drug with therapeutic potential to treat diabetes in cats" Journal of Veterinary Pharmacology and Therapeutics; vol. 41, No. 2, Apr. 1, 2018, p. 266-273.
Carlos G Santos-Gallego et al.: "Empagliflozin Ameliorates Adverse Left Ventricular Remodeling in Nondiabetic Heart Failure by Enhancing Myocardial Energetics" Journal of the American College of Cardiology; vol. 73, No. 15, Apr. 1, 2019, p. 1931-1944.
Koichiro Matsumura et al.:Effect of sodium glucose cotransporter 2 inhibitors on cardiac function and cardiovascular outcome: A systematic review Cardiovascular Ultrasound, vol. 17, No. 1, Nov. 13, 2019.
Custodio Joaquim Silva Jr et al.: "SGLT2 inhibition and heart failure-current concepts", Heart Failure Reviews, vol. 23, No. 3, Apr. 28, 2018, p. 409-418.
C. J. L. Little et al.:"Heart failure is common in diabetic cats: findings from a retrospective case-controlled study in first-opinion practice", Journal of Small Animal Practice; vol. 49, No. 1, Jan. 1, 2008, p. 17-25.
C. E. Atkins et al.:"Risk factors, clinical signs, and survival in cats with a clinical diagnosis of idiopathic hypertrophic cardiomyopathy: 74 cases (1985-1989)", J Am Vet Med Assoc. 1992, 201(4): 613-618.

(Continued)

*Primary Examiner* — Jonathan S Lau
(74) *Attorney, Agent, or Firm* — Katrina Bergbauer

(57) ABSTRACT

The present invention is directed to the use of one or more SGLT-2 inhibitors or pharmaceutically acceptable forms thereof for the prophylaxis and/or treatment of one or more cardiac diseases in feline animals.

17 Claims, 1 Drawing Sheet

(56) References Cited

OTHER PUBLICATIONS

L. M. Freeman et al.: "Feline Hypertrophic Cardiomyopathy: A Spontaneous Large Animal Model of Human HCM", Cardiol Res. 2017, 8(4): 139-142.

J. J. V. McMurray et al.: "A trial to evaluate the effect of the sodium-glucose co-transporter 2 inhibitor dapagliflozin on morbidity and mortality in patients with heart failure and reduced left ventricular ejection fraction (DAPA-HF)", Eur. J. Heart Fail. 2019, 21: 665-675.

J. R. Payne et al.: "Prognostic indicators in cats with hypertrophic cardiomyopathy", J Vet Intern Med. 2013, 27(6): 1427-1436.

J. R. Payne et al.: "Cardiomyopathy prevalence in 780 apparently healthy cats in rehoming centres (the CatScan study)", J Vet Cardiol. 2015, 17 (Suppl1): S244-S257.

J. E. Rush et al.: "Population and survival characteristics of cats with hypertrophic cardiomyopathy: 260 cases (1990-1999)", J Am Vet Med Assoc. 2002, 220(2): 202-207.

Anker, Stefan D., et al. "Empagliflozin in heart failure with a preserved ejection fraction." New England Journal of Medicine 385.16 (2021): 1451-1461.

Supplement to: Anker, Stefan D., et al. "Empagliflozin in heart failure with a preserved ejection fraction." New England Journal of Medicine 385.16 (2021): 1451-1461.

Mahmood, Iftekhar. "Application of allometric principles for the prediction of pharmacokinetics in human and veterinary drug development." Advanced drug delivery reviews 59.11 (2007): 1177-1192.

Yasuko Bando, et al. "Pathogenesis and molecular mechanisms of heart failure in diabetes What is diabetic cardiomyopathy? one." 14 Cardiac vol. 52 No. 1 (2020).

Borgeat, Kieran, et al. "Time spent with cats is never wasted: lessons learned from feline acromegalic cardiomyopathy, a naturally occurring animal model of the human disease." PLOS One 13.3 (2018): e0194342.

\* cited by examiner

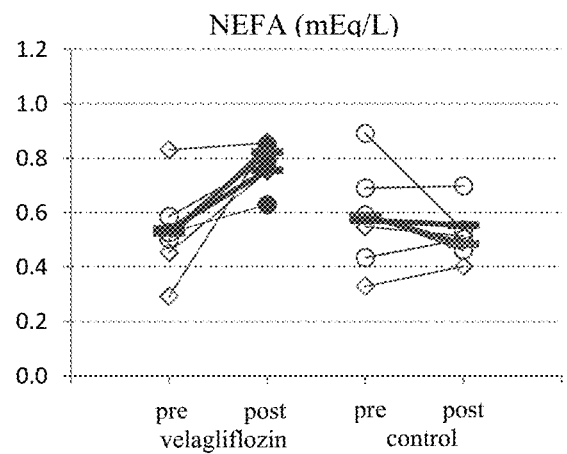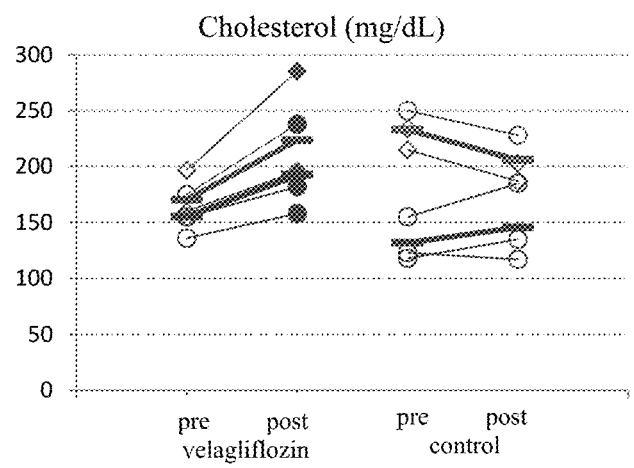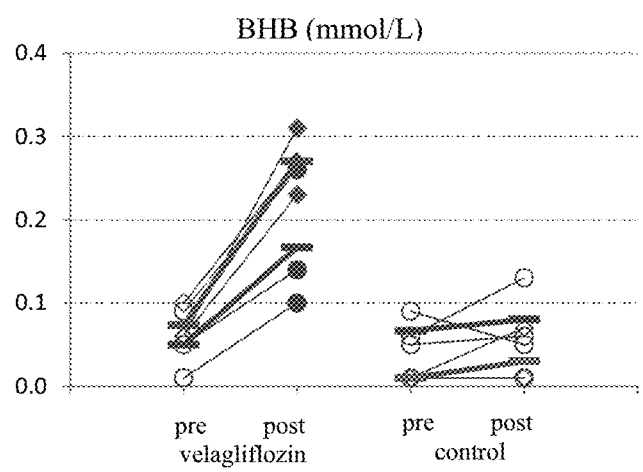

USE OF SGLT-2 INHIBITORS FOR THE PREVENTION AND/OR TREATMENT OF CARDIAC DISEASES IN FELINES

FIELD OF THE INVENTION

The invention relates to the field of medicine, in particular to the field of veterinary medicine. The invention relates to the use of SGLT-2 inhibitors or a pharmaceutically acceptable form thereof in the prevention and/or treatment of cardiac diseases in felines.

BACKGROUND INFORMATION

Heart disease is one of the most common diseases of pet cats, affecting 10-15% of all cats (Freeman et al., Cardiol Res. 2017, 8(4): 139-142; Payne J R et al., J Vet Cardiol. 2015, 17(Supp 11): S244-S257).

Feline heart diseases are classified in congenital and acquired heart diseases. The majority of heart diseases are chronic, incurable and progress over time. After a subclinical stage, clinical signs of heart failure and ultimately cardiac death may occur. Typical symptoms for a heart disease are: poor general condition, weakness, lethargy, depression, anorexia, tachycardia, tachypnoe, dyspnoe, congestion, oedema, a low peripheral blood pressure and acute posterior paresis or paralysis. Cardiomyopathies are the most common heart diseases in cats. They are classified in primary cardiomyopathies (Hypertrophic Cardiomyopathy (HC/HCM/HOCM), Restrictive Cardiomyopathy (RCM), Unclassified Cardiomyopathy (UCM), Arrhythmogenic Right Ventricular Cardiomyopathy (ARVC) and Dilated Cardiomyopathy (DCM), which is very rare in cats) and in secondary cardiomyopathies due to nutritional disorders (taurine deficiency), metabolic disorders (hyperthyroidism, acromegaly), infiltrative processes (neoplasia, amyloidosis) and inflammatory processes (toxins, immune reactions, infectious agents). The classification of the cardiomyopathy is based on echocardiographic measurements. Cats are most commonly affected by Hypertrophic Cardiomyopathy (HCM), with a prevalence of 10-15% in the general pet cat population. However, due to an inheritant form, breeds such as the Maine Coon cat, Persian, Ragdoll, and Sphynx are at higher risk.

Although heart disease is common in cats, atherosclerosis, which is a major risk factor for the development of heart failure in humans, is notably absent in cats. This is related, at least in part, to the fact that these species have high high-density lipoprotein concentrations (Freeman et al., Cardiol Res. 2017, 8(4): 139-142). In contrast to humans, in cats cardiomyopathies are thought to be the main reason for feline heart failure although not much seems to be known about the etiology of the different forms of disease.

Clinical studies have shown a median survival time in cats with HCM ranging from 92 to 2,153 days, depending on the predominant clinical signs of the population studied (i.e., asymptomatic vs. congestive heart failure (CHF) vs. arterial thromboembolism (ATE) (Atkins C E et al., J Am Vet Med Assoc. 1992, 201(4): 613-618; Rush J E et al., J Am Vet Med Assoc. 2002, 220(2): 202-207; Payne J R et al., J Vet Intern Med. 2013, 27(6): 1427-1436). Reported median survival times for cats with HCM and heart failure, for example, range from only 92 to 563 days.

WO 2011/153953 discloses crystalline forms of benzyl-benzene SGLT-2 inhibitors and mentions among others the treatment of chronic heart failure in humans.

Yet, SGLT2 inhibitors have been used in clinical trials on different subsets of human patients suffering from heart failure. However, such forms of cardiomyopathies in human patients are defined as exclusion criteria for trial participation (McMurray J J V et al., Eur. J. Heart Fail. 2019; 21: 665-675; see page 667, table 1, item 9).

Further prior art is as follows:

US 2019/076395 discloses the use of certain SGLT-2 inhibitors, such as ertugliflozin or a pharmaceutically acceptable salt or a co-crystal thereof, for treating, reducing the risk of and/or preventing heart failure, myocardial infarction, cardiovascular disease or cardiovascular death in animals without type 2 or type 1 diabetes mellitus, or in animals with pre-diabetes, or in animals with type 2 or type 1 diabetes mellitus or prediabetes.

US 2015/164856 discloses one or more SGLT2 inhibitors or pharmaceutically acceptable forms thereof for use in the treatment and/or prevention of a metabolic disorder in a feline animal, preferably wherein the metabolic disorder is one or more selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained.

Hoenig M et al. (J Vet Pharmacol Therapeutics 2018, 41(2): 266-273) discloses the effects of SGLT-2 inhibitor velagliflozin with the therapeutic potential to treat diabetes in cats.

US 2016/000816 discloses certain SGLT-2 inhibitors for treating and/or preventing oxidative stress, for example in patients with type 1 or type 2 diabetes, as well as to the use of such SGLT-2 inhibitors in treatment and/or prevention of cardiovascular diseases in patients, for example type 1 or type 2 diabetes patients.

US 2017/266152 discloses methods for preventing or treating acute or chronic heart failure and for reducing the risk of cardiovascular death, hospitalization for heart failure and other conditions in patients with preserved or reduced ejection fraction by administering empagliflozin to the patient.

US 2011/098240 discloses a pharmaceutical composition comprising a SGLT2 inhibitor in combination with a DPP IV inhibitor which is suitable in the treatment or prevention of one or more conditions selected from type 1 diabetes mellitus, type 2 diabetes mellitus, impaired glucose tolerance and hyperglycemia.

Santos-Gallego C G et al. (J American College Cardiol 2019, 73(15): 1931-1944) discloses that empagliflozin ameliorates adverse left ventricular remodeling in non-diabetic heart failure by enhancing myocardial energetics.

Matsumura K et al. (Cardiovascular Ultrasound 2019, 17(1): 26) discloses the effect of SGLT-2 inhibitors on cardiac function and cardiovascular outcome.

Silva Custodio Jr J et al. (Heart Failure Reviews 2018, 23(3): 409-418) discloses SGLT-2 inhibition and heart failure current concepts.

Little C J L et al., (J Small Anim Prac 2008, 49(1): 17-25) discloses that heart failure is common in diabetic cats: findings from a retrospective case-controlled study in first-opinion practice.

SUMMARY OF THE INVENTION

The present invention concerns one or more SGLT-2 inhibitors or pharmaceutically acceptable forms thereof for use in a method of prevention and/or treatment of one or more cardiac diseases in feline animals A corresponding method of preventing and/or treating one or more cardiac diseases in feline animals, comprising administering one or more SGLT-2 inhibitors to such feline animals, as well as the corresponding use of one or more SGLT-2 inhibitors for the preparation of a medicament for the prevention and/or treatment of one or more cardiac diseases in feline animals, are also intended to be comprised by the present invention.

In one aspect, the present invention also concerns the one or more SGLT-2 inhibitors or pharmaceutically acceptable forms thereof for the uses as herein disclosed and/or claimed, wherein the one or more cardiac diseases are selected from the group consisting of: heart failure, heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to anythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or anythmogenic right ventricular cardiomyopathy (ARVC); preferably selected from the group consisting of: heart failure due to one or more cardiomyopathies, heart failure due to hypertrophic cardiomyopathy (HCM), hypertrophic cardiomyopathy (HCM).

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In one aspect, the present invention also concerns the one or more SGLT-2 inhibitors or pharmaceutically acceptable forms thereof for the uses as herein disclosed and/or claimed, wherein the one or more cardiac diseases are selected from the group consisting of: heart failure due to one or more cardiomyopathies, heart failure due to hypertrophic cardiomyopathy (HCM), heart failure due to restrictive cardiomyopathy (RCM), heart failure due to dilated cardiomyopathy (DCM), heart failure due to unclassified cardiomyopathy (UCM), heart failure due to anythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and/or anythmogenic right ventricular cardiomyopathy (ARVC).

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In one aspect, the present invention also concerns the one or more SGLT-2 inhibitors or pharmaceutically acceptable forms thereof for the uses as herein disclosed and/or claimed, wherein the one or more cardiac diseases are selected from the group consisting of: heart failure due to hypertrophic cardiomyopathy (HCM), hypertrophic cardiomyopathy (HCM).

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In another aspect, the present invention also concerns the one or more SGLT-2 inhibitors or pharmaceutically acceptable forms thereof for the uses as herein disclosed and/or claimed, wherein the one or more SGLT-2 inhibitors are glucopyranosyl-substituted benzene derivatives.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the one or more SGLT-2 inhibitors are selected from the group consisting of:

(1) a glucopyranosyl-substituted benzene derivative of the formula (1)

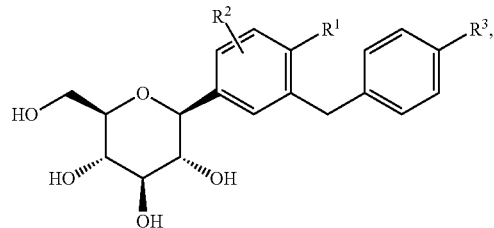

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxycyclohexyl, ethinyl, ethoxy, difluoromethyl, trifluoromethyl, pentafluoroethyl, 2-hydroxylethyl, hydroxymethyl, 3-hydroxypropyl, 2-hydroxy-2-methyl-prop-1-yl, 3-hydroxy-3-methylbut-1-yl, 1-hydroxy-1-methyl-ethyl, 2,2,2-trifluoro-1-hydroxy-1-methyl-ethyl, 2,2,2-trifluoro- 1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

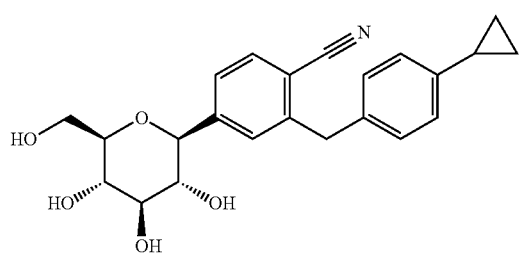 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

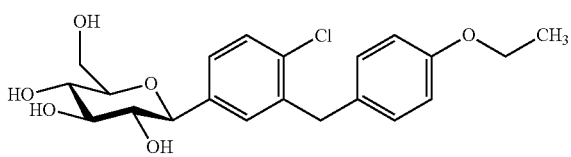

(4) Canagliflozin, represented by formula (4):

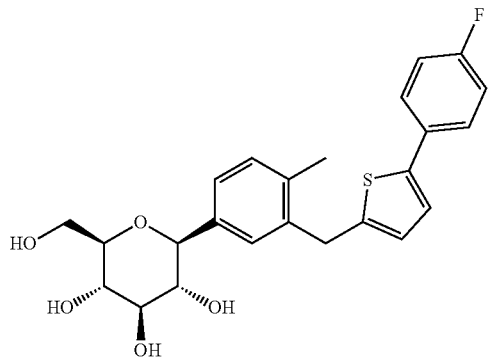 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

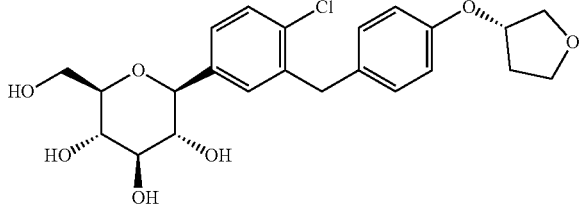 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

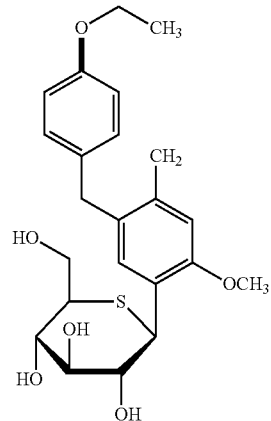

(7) Tofogliflozin, represented by formula (7):

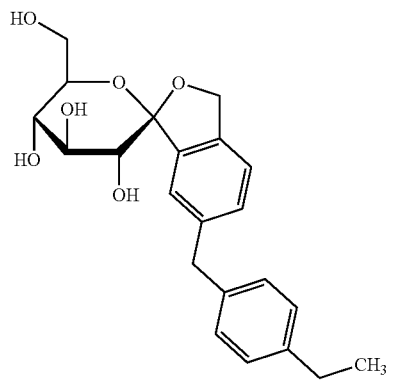

(8) Ipragliflozin, represented by formula (8):

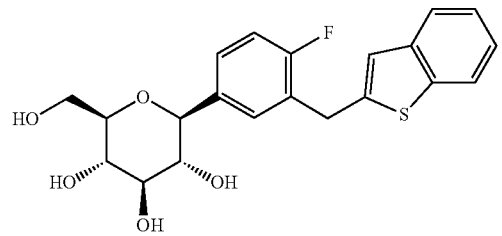 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

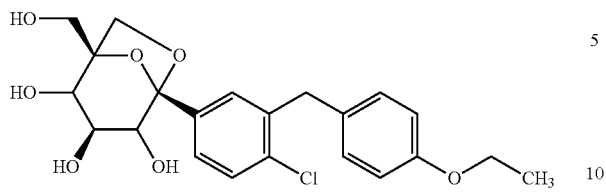

(10) Atigliflozin, represented by formula (10):

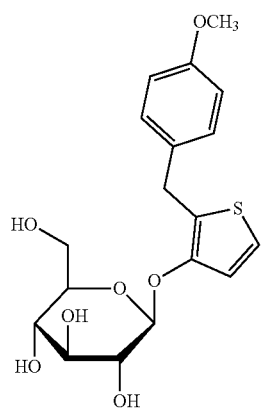

(11) Remogliflozin, represented by formula (11):

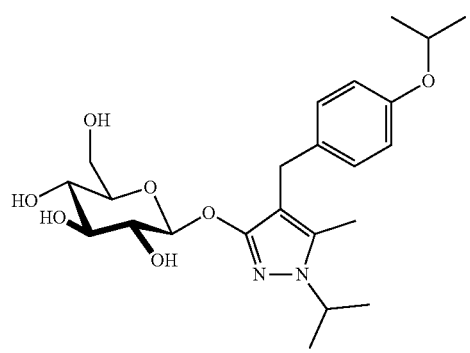

(11A) Remogliflozin etabonate, represented by formula (11A):

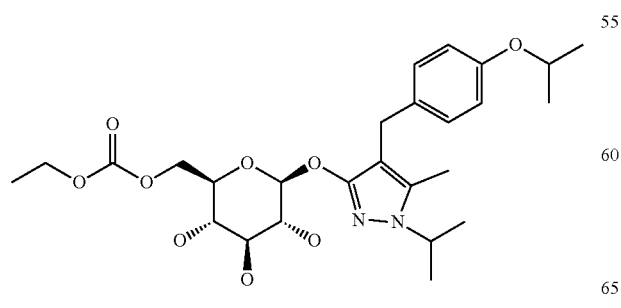

(12) a thiophene derivative of the formula (12)

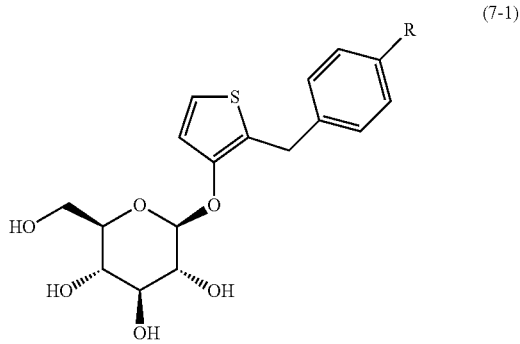

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

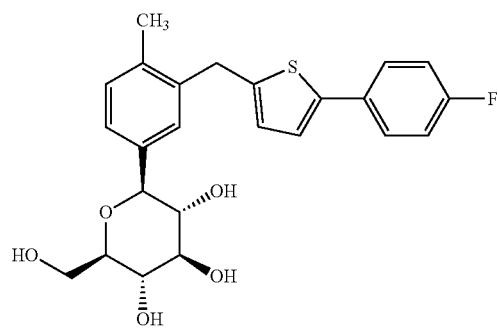 [SMILES: Cc1ccc([C@@H]2O[C@H](CO)[C@@H](O)[C@H](O)[C@H]2O)cc1Cc1ccc(-c2ccc(F)cc2)s1]

(14) a spiroketal derivative of the formula (14):

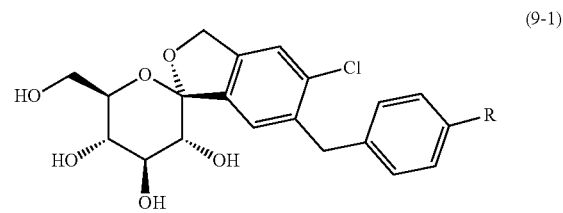

wherein R denotes methoxy, trifluoromethoxy, ethoxy, ethyl, isopropyl or tert. butyl;

(15) a pyrazole-O-glucoside derivative of the formula (15)

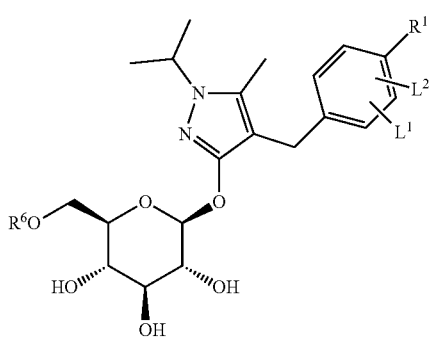

wherein
R¹ denotes $C_{1-3}$-alkoxy,
L¹, L² independently of each other denote H or F,
R⁶ denotes H, $(C_{1-3}$-alkyl)carbonyl, $(C_{1-6}$-alkyl)oxycarbonyl, phenyloxycarbonyl, benzyloxycarbonyl or benzylcarbonyl;

(16) Sotagliflozin, represented by formula (16):

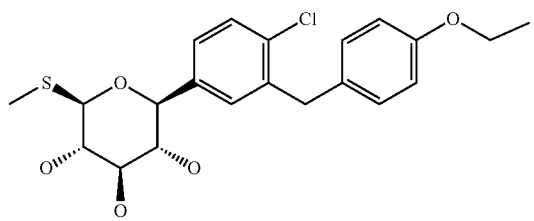 [SMILES: CCOc1ccc(Cc2cc([C@@H]3O[C@H](SC)[C@@H](O)[C@H](O)[C@H]3O)ccc2Cl)cc1]

(17) Sergliflozin, represented by formula (17):

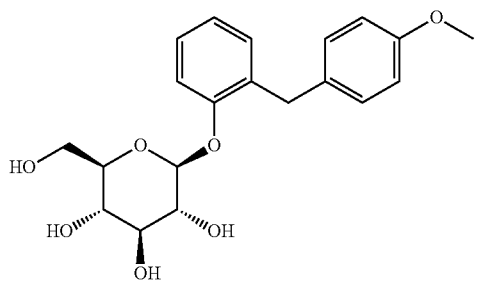

(18) a compound represented by formula (18):

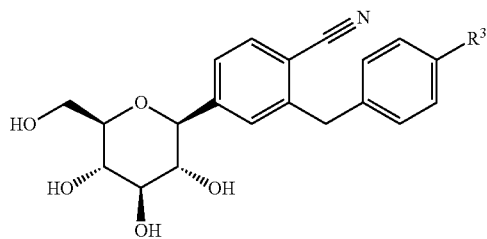

wherein
R³ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxyethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano, and wherein R³ is preferably selected from cyclopropyl, ethyl, ethinyl, ethoxy, (R)-tetrahydrofuran-3-yloxy or (S)-tetrahydrofuran-3-yloxy; and R³ most preferably is cyclopropyl,
or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl;

(19) Bexagliflozin, represented by formula (19):

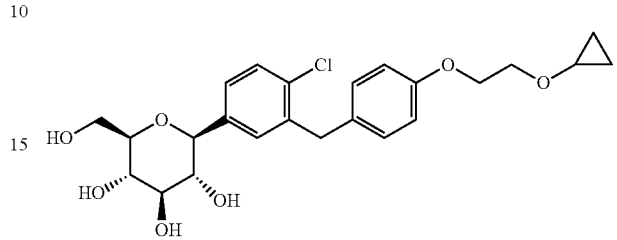

(20) Janagliflozin, represented by formula (20):

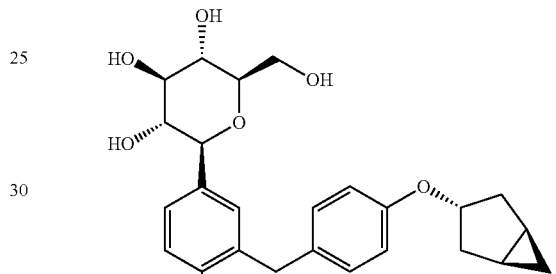

(21) Rongliflozin,
(22) Wanpagliflozin,

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the pharmaceutically acceptable form thereof is a crystalline complex between the one or more SGLT2 inhibitors and one or more amino acids, preferably proline, more preferably L-proline; and most preferably is co-crystal of the one or more SGLT2 inhibitors, L-proline and crystalline water.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the feline animal is a feline patient in need of such prevention and/or treatment; and preferably is a cat in need of such prevention and/or treatment, more preferably a non-diabetic cat in need of such prevention and/or treatment.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the one or more SGLT-2 inhibitors are administered orally, parenterally, intravenously, subcutaneously or intramuscularly, preferably orally.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the one or more SGLT-2 inhibitors are to be administered at a dose of 0.01 mg/kg bodyweight to 10 mg/kg bodyweight, preferably at a dose of 0.01 mg/kg bodyweight to 5 mg/kg bodyweight, more preferably at a dose of 0.01 mg/kg bodyweight to 4 mg/kg bodyweight, even more preferably at a dose of 0.01 mg/kg bodyweight to 3 mg/kg bodyweight, even more preferably at a dose of 0.01 mg/kg bodyweight to 2 mg/kg bodyweight, even more preferably at a dose of 0.01 mg/kg bodyweight to 1 mg/kg bodyweight, even more preferably at a dose of 0.1 mg/kg bodyweight to 1 mg/kg bodyweight, most preferably at a dose of 0.5 mg/kg bodyweight to 1 mg/kg bodyweight.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein such one or more SGLT2 inhibitors or pharmaceutically acceptable forms thereof is to be administered only once or twice per day.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the one or more SGLT-2 inhibitors is velagliflozin and velagliflozin is to be administered as single SGLT-2 inhibitor, preferably orally, more preferably once or twice per day at a dose of 0.1 mg/kg bodyweight to 1 mg/kg bodyweight, even more preferably at a dose of 0.5 mg/kg bodyweight to 1 mg/kg bodyweight.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the one or more SGLT-2 inhibitors are to be administered before, after or concomitantly with administering one or more other active pharmaceutical ingredients, preferably diuretics, such as furosemide, torasemide or spironolactone; beta-blockers, such as atenolol or propranolol; calcium-channel blockers, such as diltiazem; ACE inhibitors, such as benazepril, ramipril or enalapril; angiotensin receptors blockers, such as telmisartan; antiarrhythmic agents, such as flecainide; platelet agglutination inhibitors, such as clopidogrel; nonsteroidal anti-inflammatory drugs (NSAIDs), such as aspirin; anticoagulants, such as coumarins (vitamin K antagonists), (low molecular weight) heparin, synthetic pentasaccharide inhibitors of factor Xa, as well as direct factor Xa inhibitors and/or direct thrombin inhibitors; and/or calcium-channel sensitizers and/or positive inotropes, such as pimobendan and/or digitalis alkaloids.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

In yet another aspect, the present invention also concerns the one or more SGLT-2 inhibitors or pharmaceutically acceptable forms thereof for the uses as herein disclosed and/or claimed, wherein the preventive and/or therapeutic effect is characterized by one or more of the following clinical and/or biochemical parameters:

improved cardiometabolic efficiency, characterized by an increased ratio of [cardiac output/metabolic substrate consumed] and/or characterized by an increased ratio of [cardiac output/oxygen consumed];

increase of the production of ketone bodies in the liver, characterized by increased plasma levels of 3-hydroxybutyric acid and/or the corresponding acylcarnitines i.e. hydroxybutyiylcarnitine and increased plasma levels of one or more of the branched-chain amino acids (valine, leucine and isoleucine);

improved cardiac function by achieved reduced pre- and/or afterload, improved arterial wall structure function;

improved echocardiographic parameters, such as decreased LA (Left atrium dimension measured as right parasternal short-axis), LA/Ao (left atrium to aorta ratio; Ao=Aortic root diameter), IVSd (interventricular septal end diastolic dimension, i.e. the thickness of the interventricular septum), and/or LAD (Left atrium measured as right parasternal long-axis), and improved cardiac biomarkers, such as decreased NT-proBNP (N-terminal prohormone of brain natriuretic peptide) and/or decreased cTnI (cardiac Troponin I), as well as improved heart murmur;

delayed onset of different phenotypes of cardiomyopathies, preferably at least by 1, 2, 3, 4, 5, 6, 7, 8, 9, 10, 11, 12, 13, 14, 15 or more months, or even stopped progression of different phenotypes of cardiomyopathies;

longer time of survival, preferably at least by 1, 2, 3, 4, 5, 6, 7, 8, 9, 10, 11, 12, 13, 14, 15 or more months, and/or delay of next episode of heart failure, preferably at least by 1, 2, 3, 4, 5, 6, 7, 8, 9, 10, 11, 12, 13, 14, 15 or more months, and/or lower level of cardiac mortality and/or morbidity;

higher quality of life.

A corresponding method of preventing and/or treating one or more cardiac diseases in feline animals, comprising administering one or more SGLT-2 inhibitors to such feline animals as herein disclosed and/or claimed, as well as the corresponding use of one or more SGLT-2 inhibitors for the preparation of a medicament for the prevention and/or treatment of one or more cardiac diseases in feline animals as herein disclosed and/or claimed, are also intended to be comprised by the present invention.

The present invention further concerns a pharmaceutical composition comprising one or more SGLT2 inhibitors or pharmaceutically acceptable forms thereof as herein disclosed and/or claimed for use as herein disclosed and/or claimed.

A corresponding method of preventing and/or treating one or more cardiac diseases in feline animals, comprising administering one or more SGLT-2 inhibitors to such feline animals, as well as the corresponding use of one or more SGLT-2 inhibitors for the preparation of a medicament for the prevention and/or treatment of one or more cardiac diseases in feline animals, are also intended to be comprised by the present invention.

The advantages according to the present invention are one or more of the following:

Improved cardiometabolic efficiency by means of SGLT-2 inhibition in cats with cardiac diseases caused by the unexpected increase of the production of ketone bodies in the liver of cats (which can be used as an energy source by heart cells), which is not the case with the same compound in other species, such as horses, and which helps a failing feline heart to cope with the impaired cardiac functionality independent of the cause of feline heart failure and phenotype of cardiomyopathy Improved cardiac function in cats with cardiac diseases by achieved reduced pre- and/or afterload, improved arterial wall structure function, thereby delaying or even stopping the progression of different phenotypes of cardiomyopathies, which ultimately lead to heart failure and cardiac death Improved echocardiographic parameters, such as decreased LA (Left atrium dimension measured as right parasternal short-axis), LA/Ao (left atrium to aorta ratio; Ao=Aortic root diameter), IVSd (interventricular septal end diastolic dimension, i.e. the thickness of the interventricular septum), and/or LAD (Left atrium measured as right parasternal long-axis), and improved cardiac biomarkers, such as decreased NTproBNP (N-terminal prohormone of brain natriuretic peptide) and/or decreased cTnI (cardiac Troponin I), as well as improved heart murmur;

Longer time of survival of cats with cardiac diseases with less or even no clinical signs of cardiac diseases, preferably at least by 1, 2, 3, 4, 5, 6, 7, 8, 9, 10, 11, 12, 13, 14, 15 or more months, and/or delay of next episode of heart failure, preferably at least by 1, 2, 3, 4, 5, 6, 7, 8, 9, 10, 11, 12, 13, 14, 15 or more months, and/or lower level of cardiac mortality and/or morbidity Delay of onset of clinical symptoms in cats with cardiac diseases, preferably at least by 1, 2, 3, 4, 5, 6, 7, 8, 9, 10, 11, 12, 13, 14, 15 or more months, and/or delayed onset of different phenotypes of cardiomyopathies, preferably at least by 1, 2, 3, 4, 5, 6, 7, 8, 9, 10, 11, 12, 13, 14, 15 or more months, or even stopped progression of different phenotypes of cardiomyopathies Higher quality of life of cats with cardiac diseases

DETAILED DESCRIPTION OF THE INVENTION

Before the embodiments of the present invention are described in further detail, it shall be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was usually omitted from the description and claims Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

In cats, the most commonly seen sign of heart failure is the development of difficult breathing (dyspnoea) and/or more rapid breathing (tachypnoea). This is generally caused by either a build-up of fluid in the chest cavity around the lungs (called a pleural effusion), or due to a build-up of fluid within the lungs themselves (called pulmonary oedema). Along with breathing difficulties, cats may have cold extremities (e.g., ears and paws), and may have pale mucous membranes (gums and eyes) suggesting poor circulation. Occasionally, the mucous membranes of the mouth and eyes, and even the skin, may show signs of cyanosis (a bluish colour). All these clinical signs of heart failure are improved in cats after treatment with SGLT2 inhibitors or clinically relevant delayed in occurrence as compared to the untreated course of the disease development. Another sign which can occur in cats affected by heart diseases as cardiomyopathy and may sometimes be the first indicator of underlying heart disease, is the development of what is known as 'feline aortic thromboembolism' (FATE). A thrombus (blood clot) may develop within one of the heart chambers (usually left atrium) in a cat with cardiomyopathy. This occurs mainly because the blood is not flowing normally through the heart. The thrombus, or clot, is initially attached to the wall of the heart, but may become dislodged and be carried into the blood leaving the heart. A thrombus that moves into the blood circulation is called an embolus, hence the term 'thromboembolism'. Once in the circulation, these emboli can lodge in small arteries and obstruct the flow of blood to regions of the body. Although this can happen at a number of different sites, it more commonly occurs towards the end of the major artery that leaves the heart (the aorta) as it divides to supply blood to the back legs. This complication is seen most commonly with HCM, and will cause a sudden onset of paralysis to one or both back legs, with severe pain and considerable distress. Also, this clinical sign of heart failure is improved in cats after treatment with SGLT2 inhibitors or clinically relevant delayed in occurrence as compared to the untreated course of the disease development, preferably at least by 1, 2, 3, 4, 5, 6, 7, 8, 9, 10, 11, 12, 13, 14, 15 or more months. Overall, the survival time of cats after treatment with SGLT2 inhibitors is clinically relevant increased at least by 1, 2, 3, 4, 5, 6, 7, 8, 9, 10, 11, 12, 13, 14, 15 or more months, preferably at least by 6 months, as compared to untreated cats with cardiomyopathy.

In the course of the present invention, the term "feline animal" or "feline" refers to any member of the Felidae family (i.e. a felid). It may thus belong either to the subfamily felinae or the subfamily pantherinae. The term feline animal encompasses the term cat, e.g., a domestic cat. The term domestic cat encompasses the terms *Felis catus* and *Felis silvestris catus*. Most preferably, the feline animal or feline is a cat, in particular a domestic cat.

In the course of the present invention, the term "heart disease" is synonymous with "cardiac disease" and refers to any disorder and deformities of the heart itself, which affect the heart's structure and function. There are many types of heart disease that affect different parts of the organ and occur in different ways including congenital heart diseases (e.g. septal defects, obstruction defects), arrhythmias (e g tachycardia, bradycardia and fibrillation) and cardiomyopathies.

In the course of the present invention, the term "heart failure", also known as congestive heart failure and congestive cardiac failure, refers to the pathophysiological process in which the heart cannot pump sufficiently to maintain the blood flow through the body to meet the metabolic requirements (oxygen and substrates) of peripheral tissues and organs. It can also be defined as a complex clinical syndrome that is based on abnormal structure or function of the heart and which is characterized by symptoms like exercise intolerance, dyspnoea, fatigue, fluid retention and reduced longevity. It can be divided into systolic failure, where the ejection of blood out of the heart in the systole is affected, and diastolic failure, where the heart is not able to receive enough blood in the ventricular cavities at low pressure during diastole. It is mostly a chronic disease due to a chronic work overload of the heart or developed after an acute hemodynamic stress due to fluid overload, a valvular dysfunction or a myocardial infarction.

In the course of the present invention, the term "cardiomyopathy" refers to a group of diseases that affect the heart muscle being the most common form of heart disease seen in cats, and the most common cause of heart failure. Cardiomyopathies are described according to the effect they have on the structure and function of the cardiac muscle. Types of cardiomyopathy include: hypertrophic cardiomyopathy (HCM), restrictive cardiomyopathy (RCM), unclassified cardiomyopathy (UCM), arrhythmogenic right ventricular cardiomyopathy (ARVC) and dilated cardiomyopathy (DCM). The classification is based on echocardiographic measurements.

Hypertrophic cardiomyopathy (HCM) is the most prevalent feline cardiac disorder. It affects most commonly middle-aged cats (average 6.5 years), but all ages are affected. There is a male predisposition (>75%). In humans, there is an important hereditary predisposition for HCM in 55% of cases. In people, this disorder may be congenital or acquired, and probably represents a group of diseases. Although the etiology of feline HCM is unknown, the Persian and Maine coon cat have appeared to be predisposed in some case series, suggesting a genetic influence. As is the case with systemic hypertension, hyperthyroidism, and aortic stenosis, HCM is associated with marked left ventricular hypertrophy, but in this instance, no underlying cause can be identified. Cardiac lesions are typified by severe left ventricular concentric hypertrophy and secondary left atrial dilatation. Asymmetric septal hypertrophy (ASH), present in the majority of dogs and humans with HCM, is present in only 30% of cats with HCM. Histological cardiac myofiber disarray is reported in 27% of affected cats and only in those with asymmetric septal hypertrophy. Other histological features of feline HCM include myocardial and endocardial fibrosis and narrowed coronary arteries. Dynamic aortic outflow obstruction, secondary mitral insufficiency, myocardial ischemia, and systemic arterial embolism (SAE) may complicate this syndrome. The left heart is predominately affected and clinical signs manifested as sudden death or, more commonly, acute left heart failure due to diastolic dysfunction. Pleural effusion is occasionally associated with HCM. Systolic function is usually adequate or enhanced. Stressful incidents, such as a car ride, restraint for an ECG, confrontation with a dog, or an embolic event may precipitate in left heart failure and pulmonary oedema.

A hypertrophic obstructive cardiomyopathy (HOCM) is characterized by a left ventricular hypertrophy combined with an outflow obstruction of the left ventricle into the aorta. The degree of obstruction and clinical presentation is dependent upon the extent of hypertrophy. It most commonly affects the ventricular septum, although any portion of the left ventricle can be affected.

Restrictive Cardiomyopathy (RCM) occurs when ventricular diastolic compliance is impaired (i.e., stiffness is increased) by infiltration of the endocardium, subendocardium, or myocardium by fibrous tissue or another component. In contrast to human medicine where specific causes, such as amyloidosis and eosinophilic infiltration are causes of RCM, specific causes for RCM have not been clearly defined in the cat. Without the use of invasive diagnostic procedures to directly measure left ventricular diastolic function, DTI, other indirect measures of diastolic function, or necropsy examination, it is often impossible to distinguish this disorder from the form or forms of unclassified cardiomyopathy that are idiopathic. The precise etiology of feline RCM is unknown. However, there is some evidence that it may be inflammatory in nature.

Dilated cardiomyopathy (DCM) is characterized by dilated or enlarged heart chambers and reduced contraction ability. Before 1987, DCM was one of the most common heart diseases in cats. This is suspected to have been related to a dietary deficiency of the amino acid taurine. Today DCM in cats is relatively rare, since most cat food manufacturers began adding taurine supplements to their foods, further confirming the relationship. Some breeds, such as the Burmese, Abyssinian, and Siamese, are more commonly affected by DCM, but the underlying cause in the majority of cases remains unknown. The disease will usually affect cats between the ages of 2 to 20 years, but the average age of onset is ten years old.

Unclassified Cardiomyopathy (UCM): in recent years an increasing number of cats have been identified that do not fit into any recognized disease classification using echocardiographic and pathological criteria. Typically, these cats have severe biatrial enlargement, normal left ventricles or mild hypertrophy and normal or slightly decreased systolic function, but they do not have the typical post-mortem findings of fibrosis seen in restrictive cardiomyopathy. Many cats have enlargement of the right ventricle. It is not known if these cats represent a progressive or regressive form of other known cardiomyopathic states.

Arrhythmogenic Right Ventricular Cardiomyopathy (ARVC): this form of cardiomyopathy has recently been described in cats. The etiology is unknown, however a familial form has been reported in humans. It is characterized by severe right atrial and ventricular enlargement and marked tricuspid regurgitation due to distortion of the tricuspid valve; arrhythmias are common. It is possible that cases of ARVC have previously been misdiagnosed as tricuspid valve dysplasia.

SGLT-2 inhibitors for use according to the invention include, but are not limited to, glucopyranosyl-substituted benzene derivatives, for example as described in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940, WO 2009/022020 or WO 2009/022008.

Moreover, the one or more SGLT-2 inhibitors for use according to the invention may be selected from the group consisting of the following compounds or pharmaceutically acceptable forms thereof:

(1) a glucopyranosyl-substituted benzene derivative of the formula (1)

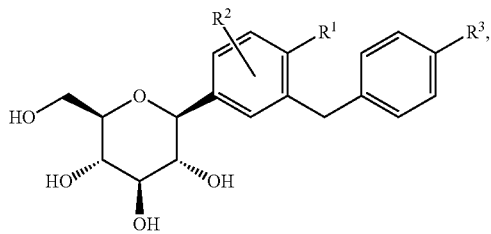

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxycyclohexyl, ethinyl, ethoxy, difluoromethyl, trifluoromethyl, pentafluoroethyl, 2-hydroxylethyl, hydroxymethyl, 3-hydroxypropyl, 2-hydroxy-2-methyl-prop-1-yl, 3-hydroxy-3-methylbut-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein $R^3$ is preferably selected from cyclopropyl, ethyl, ethinyl, ethoxy, (R)-tetrahydrofuran-3-yloxy or (S)-tetrahydrofuran-3-yloxy; and most preferably $R^3$ is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl;

(2) Velagliflozin, represented by formula (2):

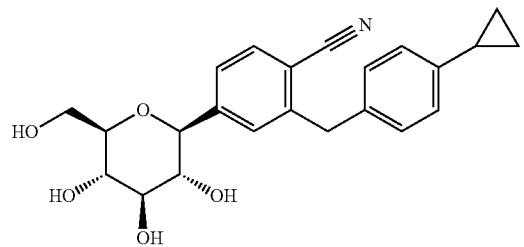 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

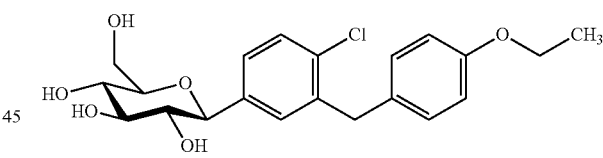

(4) Canagliflozin, represented by formula (4):

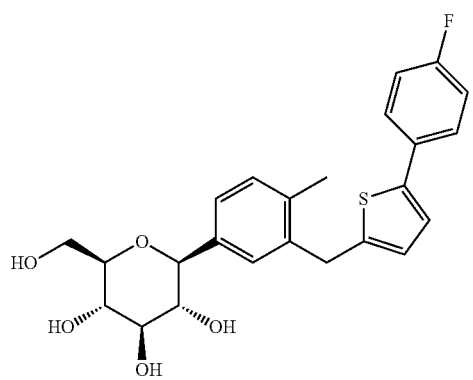 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):
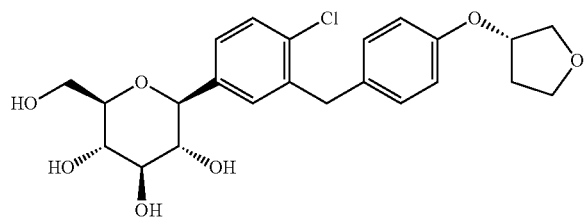 [SMILES: OC[C@H]1O[C@@H](c2ccc(Cl)c(Cc3ccc(O[C@H]4CCOC4)cc3)c2)[C@H](O)[C@@H](O)[C@@H]1O]
(6) Luseogliflozin, represented by formula (6):
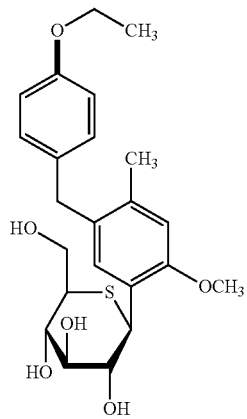
(7) Tofogliflozin, represented by formula (7):
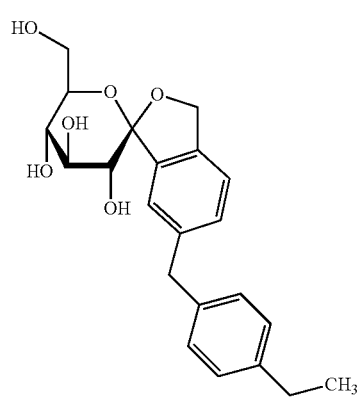
(8) Ipragliflozin, represented by formula (8):
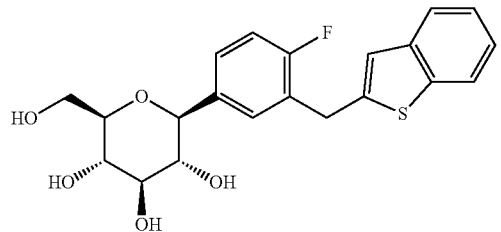 [SMILES: OC[C@H]1O[C@@H](c2ccc(F)c(Cc3cc4ccccc4s3)c2)[C@H](O)[C@@H](O)[C@@H]1O]
(9) Ertugliflozin, represented by formula (9):
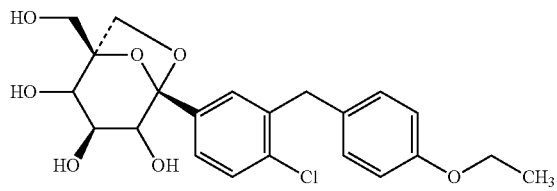 [SMILES: CCOc1ccc(Cc2cc([C@]34OC[C@](CO)(O3)C(O)[C@H](O)C4O)ccc2Cl)cc1]
(10) Atigliflozin, represented by formula (10):
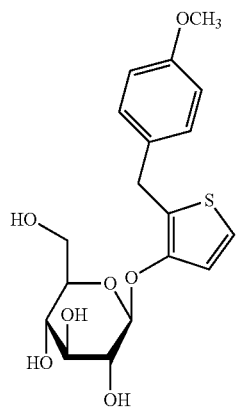
(11) Remogliflozin, represented by formula (11):
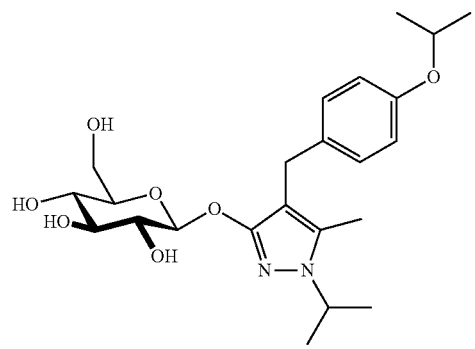
(11A) Remogliflozin etabonate, represented by formula (11A):
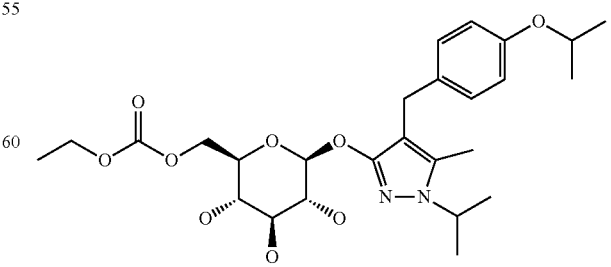

(12) a thiophene derivative of the formula (12)

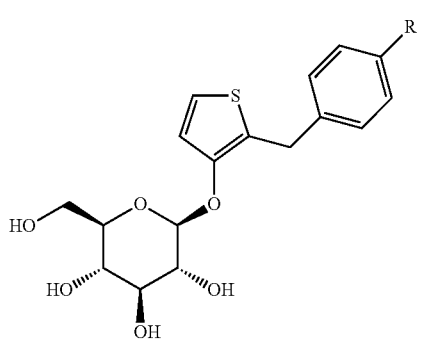

(7-1)

wherein R denotes methoxy or trifluoromethoxy;

(13) 1-(β-D-glucopyranosyl)-4-methyl-3-[5-(4-fluorophenyl)-2-thienylmethyl]benzene, represented by formula (13);

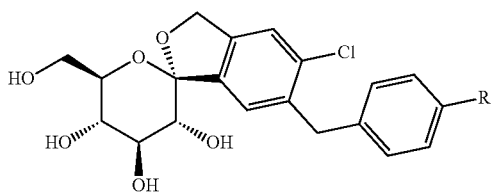

(14) a spiroketal derivative of the formula (14):

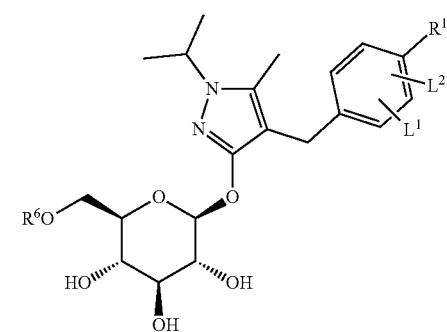

(9-1)

wherein R denotes methoxy, trifluoromethoxy, ethoxy, ethyl, isopropyl or tert. butyl;

(15) a pyrazole-O-glucoside derivative of the formula (15)

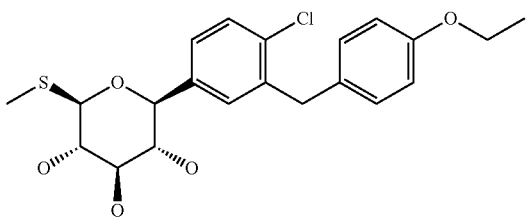

wherein
$R^1$ denotes $C_{1-3}$-alkoxy,
$L^1$, $L^2$ independently of each other denote H or F,
$R^6$ denotes H, $(C_{1-3}$-alkyl)carbonyl, $(C_{1-6}$-alkyl)oxycarbonyl, phenyloxycarbonyl, benzyloxycarbonyl or benzylcarbonyl;

(16) Sotagliflozin, represented by formula (16):

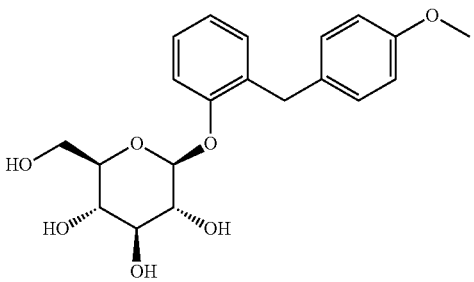 [SMILES: COc1ccc(Cc2ccccc2O[C@@H]2O[C@H](CO)[C@@H](O)[C@H](O)[C@H]2O)cc1]

(17) Sergliflozin, represented by formula (17):

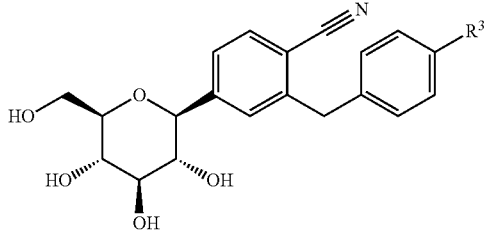

(18) a compound represented by formula (18):

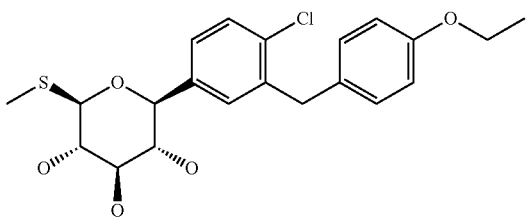

wherein
$R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano; and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl;

(19) Bexagliflozin, represented by formula (19):

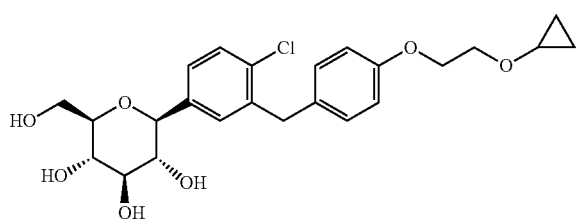 [SMILES: OC[C@H]1O[C@@H](c2ccc(Cl)c(Cc3ccc(OCCOC4CC4)cc3)c2)[C@H](O)[C@@H](O)[C@@H]1O]

(20) Janagliflozin, represented by formula (20):

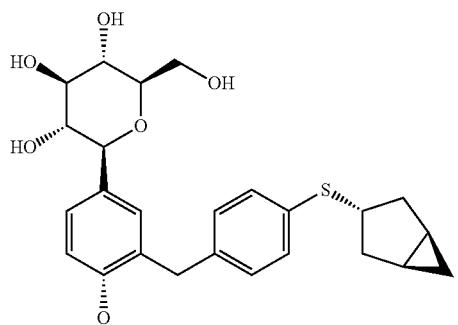

(21) Rongliflozin,
(22) Wanpagliflozin.

The term "velagliflozin" as employed herein refers to velagliflozin of the above structure as well as pharmaceutically acceptable forms thereof, including hydrates and solvates thereof, and crystalline forms thereof. The compound, methods of its synthesis and co-crystals thereof are described in WO 2007/128749, WO 2014/016381 and WO 2019/121509 for example.

The term "dapagliflozin" as employed herein refers to dapagliflozin of the above structure as well as pharmaceutically acceptable forms thereof, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example.

The term "canagliflozin" as employed herein refers to canagliflozin of the above structure as well as pharmaceutically acceptable forms thereof, including hydrates and solvates thereof, and crystalline forms thereof. The compound and methods of its synthesis are described in WO 2005/012326 and WO 2009/035969 for example. Preferred hydrates, solvates and crystalline forms are described in the patent application WO 2008/069327 for example.

The term "empagliflozin" as employed herein refers to empagliflozin of the above structure as well as pharmaceutically acceptable forms thereof, including hydrates and solvates thereof, and crystalline forms thereof.

The compound and methods of its synthesis are described in WO 2005/092877, WO 2006/120208 and WO 2011/039108 for example. A preferred crystalline form is described in the patent applications WO 2006/117359 and WO 2011/039107 for example.

The term "atigliflozin" as employed herein refers to atigliflozin of the above structure as well as pharmaceutically acceptable forms thereof, including hydrates and solvates thereof, and crystalline forms thereof. The compound and methods of its synthesis are described in WO 2004/007517 for example.

The term "ipragliflozin" as employed herein refers to ipragliflozin of the above structure as well as pharmaceutically acceptable forms thereof, including hydrates and solvates thereof, and crystalline forms thereof. The compound and methods of its synthesis are described in WO 2004/080990, WO 2005/012326 and WO 2007/114475 for example.

The term "tofogliflozin" as employed herein refers to tofogliflozin of the above structure as well as pharmaceutically acceptable forms thereof, including hydrates and solvates thereof, and crystalline forms thereof. The compound and methods of its synthesis are described in WO 2007/140191 and WO 2008/013280 for example.

The term "luseogliflozin" as employed herein refers to luseogliflozin of the above structure as well as pharmaceutically acceptable forms thereof, including hydrates and solvates thereof, and crystalline forms thereof.

The term "ertugliflozin" as employed herein refers to ertugliflozin of the above structure as well as pharmaceutically acceptable forms thereof, including hydrates and solvates thereof, and crystalline forms thereof. The compound is described for example in WO 2010/023594.

The term "remogliflozin" as employed herein refers to remogliflozin of the above structure as well as pharmaceutically acceptable forms thereof, including prodrugs of remogliflozin, in particular remogliflozin etabonate, including hydrates and solvates thereof, and crystalline forms thereof. Methods of its synthesis are described in the patent applications EP 1 213 296 and EP 1 354 888 for example.

The term "sergliflozin" as employed herein refers to sergliflozin of the above structure as well as pharmaceutically acceptable forms thereof, including prodrugs of sergliflozin, in particular sergliflozin etabonate, including hydrates and solvates thereof, and crystalline forms thereof. Methods for its manufacture are described in the patent applications EP 1 344 780 and EP 1 489 089 for example.

The compound of formula (16) above, i.e. sotagliflozin, and its manufacture are described for example in WO 2008/042688 or WO 2009/014970.

Preferred SGLT-2 inhibitors are glucopyranosyl-substituted benzene derivatives. Optionally, one or more hydroxyl groups of the glucopyranosyl group in such one or more SGLT-2 inhibitors may be acylated with groups selected from ($C_{1-18}$-alkyl)carbonyl, ($C_{1-18}$-alkyl)oxycarbonyl, phenylcarbonyl and phenyl-($C_{1-3}$-alkyl)carbonyl.

More preferred are glucopyranosyl-substituted benzonitrile derivatives of formula (1) as disclosed herein above. Yet more preferred are glucopyranosyl-substituted benzonitrile derivatives of formula (18):

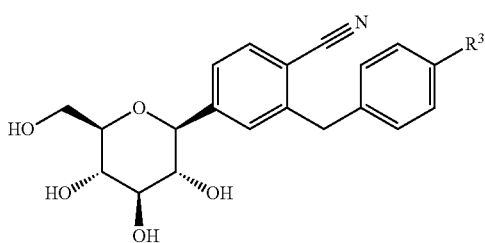

wherein $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano; and wherein $R^3$ is preferably selected from cyclopropyl, ethyl, ethinyl, ethoxy, (R)-tetrahydrofuran-3-yloxy or (S)-tetrahydrofuran-3-yloxy; and $R^3$ most preferably is cyclopropyl, or a derivative thereof wherein one or more hydroxyl groups of the β-D-glucopyranosyl group are acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Preferably, such SGLT-2 inhibitor is velaglifozin as shown in formula (2). Optionally, one or more hydroxyl groups of the β-D-glucopyranosyl group of velagliflozin may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Thus, in a preferred embodiment, the at least one SGLT-2 inhibitor according to the present invention is a glucopyranosyl-substituted benzene derivative SGLT-2 inhibitor, preferably a SGLT-2 inhibitor of formula (1), more preferably of formula (18), or yet more preferably of formula (2), i.e. velagliflozin, in each case as defined herein above.

Herein, references to SGLT-2 inhibitors and/or their use according to the invention encompass pharmaceutically acceptable forms of the SGLT-2 inhibitors, unless otherwise stated.

According to the invention, any pharmaceutically acceptable form of the SGLT-2 inhibitor, e.g. of formula (1), preferably formula (18), more preferably formula (2), may be used. E.g. a crystalline form may be used. Prodrug forms are also encompassed by the present invention.

Prodrug forms may include, e.g., esters and/or hydrates. The term "prodrug" is also meant to include any covalently bonded carrier, which releases the active compound of the invention in vivo when the prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention.

Crystalline forms for use according to the invention include a complex of an SGLT-2 inhibitor with one or more amino acids (see e.g. WO 2014/016381)—so-called co-crystals. An amino acid for such use may be a natural amino acid. The amino acid may be a proteogenic amino acid (including L-hydroxyproline), or a nonproteogenic amino acid. The amino acid may be a D- or an L-amino acid. In some preferred embodiments, the amino acid is proline (L-proline and/or D-proline, preferably L-proline). E.g., a crystalline complex/cocrystal of velagliflozin with proline (e.g. L-proline) and crystalline water is preferred.

Thus, herein is disclosed a crystalline complex/co-crystal between one or more natural amino acids and an SGLT-2 inhibitor, e.g., a crystalline complex/co-crystal between one or more natural amino acids and a glucopyranosyl-substituted benzene derivative SGLT-2 inhibitor, preferably a SGLT-2 inhibitor of formula (1), more preferably of formula (18) or yet more preferably of formula (2) (velagliflozin).

A certain pharmaceutical activity is the basic prerequisite to be fulfilled by a pharmaceutically active agent before it is approved as a medicament on the market. However, there is a variety of additional requirements a pharmaceutically active agent has to comply with. These requirements are based on various parameters, which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions, which contain, in addition to the actual active substance, breakdown products thereof, for example. In such cases, the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronizing) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation, which always contains the specified amount of active substance in a reproducible manner.

Another problem, which may arise in the grinding process for preparing the desired pharmaceutical formulation, is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance because of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be at best slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition, which is capable of improving its physical and chemical stability, gives a significant advantage over less stable forms of the same medicament.

A crystalline complex/co-crystal between a natural amino acid and an SGLT-2 inhibitor (e.g. a glucopyranosyl-substituted benzene derivative or a SGLT-2 inhibitor of formula (1), or formula (18) or, particularly, of formula (2), i.e. velaglilfozin) fulfills important requirements mentioned hereinbefore.

SGLT-2 inhibitors for use according to the invention may be prepared as pharmaceutical compositions. They may be prepared as solid or as liquid formulations. In either case, they are preferably prepared for oral administration, preferably in liquid form for oral administration (see e.g. WO 2017/032799). The SGLT-2 inhibitors may, however, also be prepared, e.g., for parenteral administration. Solid formulations include tablets, granular forms, and other solid forms such as suppositories. Among solid formulations, tablets and granular forms are preferred.

Pharmaceutical compositions within the meaning of the present invention may comprise an SGLT-2 inhibitor according to the present invention and one or more excipients. Any excipient that allows for, or supports, the intended medical effect may be used. Such excipients are available to the skilled person. Useful excipients are for example antiadherents (used to reduce the adhesion between the powder (granules) and the punch faces and thus prevent sticking to tablet punches), binders (solution binders or dry binders that hold the ingredients together), coatings (to protect tablet ingredients from deterioration by moisture in the air and make large or unpleasant-tasting tablets easier to swallow), disintegrants (to allow the tablet to break upon dilution), fillers, diluents, flavours, colours, glidants (flow regulators—to promote powder flow by reducing interparticle friction and cohesion), lubricants (to prevent ingredients from clumping together and from sticking to the tablet punches or capsule filling machine), preservatives, sorbents, sweeteners etc.

Formulations according to the invention, e.g. solid formulations, may comprise carriers and/or disintegrants selected from the group of sugars and sugar alcohols, e g mannitol, lactose, starch, cellulose, microcrystalline cellulose and cellulose derivatives, e.g. methylcellulose, and the like.

Manufacturing procedures for formulations suitable for felines are known to the person skilled in the art, and for solid formulations comprise, e.g., direct compression, dry granulation and wet granulation. In the direct compression process, the active ingredient and all other excipients are placed together in a compression apparatus that is directly applied to press tablets out of this material. The resulting tablets can optionally be coated afterwards in order to protect them physically and/or chemically, e.g. by a material known from the state of the art.

A unit for administration, e.g. a single liquid dose or a unit of a solid formulation, e.g. a tablet, may comprise 0.1 mg to 10 mg, or e.g. 0.3 mg to 1 mg, 1 mg to 3 mg, 3 mg to 10 mg; or 5 to 2500 mg, or e.g. 5 to 2000 mg, 5 mg to 1500 mg, 10 mg to 1500 mg, 10 mg to 1000 mg, or 10-500 mg of an SGLT-2 inhibitor for use according to the invention. As the skilled person would understand, the content of the SGLT-2 inhibitor in a solid formulation, or any formulation as disclosed herein for administration to a feline animal, may be increased or decreased as appropriate in proportion to the body weight of the feline animal to be treated.

In one embodiment, a pharmaceutical composition for use according to the invention is designed for oral or parenteral administration, preferably for oral administration. Especially the oral administration is ameliorated by excipients, which modify the smell and/or haptic properties of the pharmaceutical composition for the intended patient, e.g. as described.

When the SGLT-2 inhibitor for use according to the invention is formulated for oral administration, it is preferred that excipients confer properties, e.g. palatability and/or chewability that render the formulation suitable for administration to a feline animal.

Also preferred are liquid formulations. Liquid formulations may be, e.g., solutions, syrups or suspensions. They may be administered directly to the felines or may be mixed with the food and/or drink (e g drinking water, or the like) of the feline animal One advantage of a liquid formulation (similar to a formulation in granular form), is that such a dosage form allows precise dosing. For example, the SGLT-2 inhibitor may be dosed precisely in proportion to the body mass of a feline animal Typical compositions of liquid formulations are known to the person skilled in the art.

A practitioner skilled in the art can determine suitable doses for the uses of the present invention. Preferred units dosing units include mg/kg bodyweight, i.e. mg SGLT-2 inhibitor per body mass of the feline animal. An SGLT-2 inhibitor of the invention may, e.g., be administered in doses of 0.01-10 mg/kg bodyweight per day, e.g. 0.01-5 mg/kg bodyweight per day, e.g. 0.01-4 mg/kg bodyweight per day, e.g. 0.01-3 mg/kg bodyweight per day, e.g. 0.01-2 mg/kg bodyweight per day, e.g. 0.01-1.5 mg/kg bodyweight per day, e.g., 0.01-1 mg/kg bodyweight per day, e.g. 0.01-0.75 mg/kg bodyweight per day, e.g. 0.01-0.5 mg/kg bodyweight per day, e.g. 0.01-0.4 mg/kg bodyweight per day; or 0.1 to 3.0 mg/kg bodyweight per day, preferably from 0.2 to 2.0 mg/kg bodyweight per day, more preferably from 0.1 to 1 mg/kg bodyweight per day or from 0.5 to 1 mg/kg bodyweight per day. In another preferred embodiment, the dose is 0.01-0.5 mg/kg bodyweight per day, more preferably 0.02-0.4 mg/kg bodyweight per day, e.g. 0.03-0.3 mg/kg bodyweight per day.

A practitioner skilled in the art is able to prepare an SGLT-2 inhibitor of the invention for administration according to a desired dose.

BRIEF DESCRIPTION OF THE DRAWINGS

FIG. 1 shows plasma non-esterified fatty acids (NEFA), cholesterol and beta-hydroxybutyrat (BHB)—individual data in cats prior to start of treatment (pre) with velagliflozin or control and at the end of the four week treatment period (post). A significant treatment effect, an increase in blood lipids (NEFA, cholesterol) and plasma concentrations of BHB is noted.

EXAMPLES

The following examples serve to further illustrate the present invention; but the same should not be construed as a limitation of the scope of the invention disclosed herein.

Example 1 Clinical Field Study

Client-owned cat patients (older than 1 year) with every possible phenotype of cardiomyopathy (HCM, RCM, UCM, DCM and ARVC) with or without clinical symptoms (e.g. congestive heart failure) are treated orally and once daily with a velagliflozin dosage of 1 mg/kg bodyweight.

During the study period the body weight, body condition score, blood pressure and the cardiovascular system (including heart rates, rhythm, presence of gallop sound or murmur and intensity) are examined on a regular basis during the visits at the site by the investigator. Additionally, thoracic radiographs (in the right lateral and dorso ventral view), echocardiography (including LV septal & free wall thickness, LVIDD, LVIDS (FS %), LA/Ao, LAD, ejection fraction) and electrocardiography are performed. In order to obtain an overview as complete as possible regular blood tests include a complete hematology (white blood cells (WBC), WBC differential, red blood cells, hemoglobin, hematocrit, Heinz bodies, platelet count), a biochemistry panel (total protein, Albumin, Globulin, Alkaline phosphatase (ALP), Alanine transaminase (ALT), Aspartate transaminase (AST), Total bilirubin, Creatinine, Blood urea nitrogen or urea (BUN), Calcium, Sodium, Potassium, Chloride, Phosphorus, Glucose, Cholesterol, Triglycerides, Fructosamine), the measurement of total T4, ketone bodies and cardiac biomarkers (Plasma NT-pro BNP, Cardiac troponin I, ST2).

Variables of interest are the number of events defined as cardiac death, cardiac related euthanasia and (re-) occurrence of congestive heart failure and the time to event (survival time of the cat patients).

The results of the clinical field trial show a significant and clinically relevant prolongation of survival time and the time to event (event was defined as cardiac death/euthanasia and (re-)occurrence of congestive heart failure) compared to placebo on top of standard of care (SoC). Additionally, clinical parameters (e.g. appetite, activity level and breathing) compared to placebo on top of SoC improve significantly.

Example 2 Exploratory Clinical Field Study

Introduction, Materials and Methods:

In an exploratory clinical field study (prospective, baseline controlled, open label and multi-site) under real world conditions, four cats were screened for eligibility for compassionate use of velagliflozin to treat cardiomyopathies and heart failure in cats. Two cats with hypertrophic cardiomyopathy (HCM) and recent heart failure were found to meet the inclusion criteria and were treated orally with the SGLT-2-Inhibitor velagliflozin at a dosage of 1 mg/kg bodyweight once per day. Due to non-compliance to treatment regime of one pet owner only one cat remained in the study over the complete planned time period of 90 days. Clinical symptoms (evaluated in a physical examination according to Good Veterinary Practice), echocardiographic parameters (always done by the same person at each visit and according to the ACVIM consensus statement guidelines for the classification, diagnosis, and management of cardiomyopathies in cats), blood parameters (evaluated by IDEXX Bioresearch Laboratories, Germany), number of events (re-occurrence of heart failure, cardiac related death or euthanasia) and time to event in days were documented at each visit on the respective Case Report Form.

Results:

Case 101 was a 10 years old, female spayed Maine Coon cat, diagnosed with hypertrophic cardiomyopathy (HCM) and previous congestive heart failure. At day 0 (study start) the cat was clinically stable, under owner care and did not receive any additional medication. During the treatment period (Day 1 until Day 90) the cat experienced no adverse event and no heart failure or pulmonary oedema re-occurred. The cat terminated the study in good general health.

TABLE 1

Clinical symptoms at Screening visit at day −7 and the following two study visits at day 45 and day 90

| Cardiological examination | Screening Visit (D − 7) | Visit 2 (D45) | Visit 3 (D90) |
| --- | --- | --- | --- |
| BPM (mmHG) | 128 | 136 | 124 |
| Resting respiratory rate | 28 | 34 | 34 |
| Heart rate | 140 | 180 | 176 |
| Presence of gallop sound | no | no | no |
| Presence of arrythmia | no | no | no |
| Presence of murmur | yes | yes | yes |
| Timing of murmur | systolic | systolic | systolic |
| Grade of murmur | 4 | 3 | 2 |
| Point of maximum intensity | left apical | left apical | left apical |

TABLE 2

Echocardiographic parameters at Screening visit at day −7 and the following two study visits at day 45 and day 90

| Echocardiographic parameters | Screening Visit (D − 7) | Visit 2 (D45) | Visit 3 (D90) |
| --- | --- | --- | --- |
| LA (mm) | 1.55 | 1.44 | 1.19 |
| LA/Ao | 1.63 | 1.36 | 1.07 |
| IVSd (mm) | 0.76 | 0.5 | 0.43 |
| LAD max (mm) | 16.3 | 13.8 | 12.6 |

LA (Left atrium dimension measured as right parasternal short-axis); Ao (Aortic root diameter); LA/Ao, left atrium to aorta ratio; IVSd (interventricular septal end diastolic dimension, i.e. the thickness of the interventricular septum); LAD (Left atrium measured as right parasternal long-axis)

TABLE 3

Cardiac biomarker at Screening visit at day −7 and the following two study visits at day 45 and day 90

| Cardiac biomarker | Screening visit(D − 7) | Visit 2 (D45) | Visit 3 (D90) |
|---|---|---|---|
| NT-proBNP (pmol/l) | 177 | 104 | 39 |

NT-proBNP (N-terminal prohormone of brain natriuretic peptide)

Conclusion:

At the Screening visit (before treatment) the pathophysiological characteristics of cat 101 exhibited a hypertrophic cardiomyopathy (HCM). HCM phenotype is characterized by increased left ventricular wall thickness (LVWT) in the absence of abnormal loading conditions capable of producing a similar degree of ventricular thickening as well as thickening of the interventricular septum (IVSd). A further characteristic of the disease is an increased left atrium (LA) as has been shown also in cat 101 at screening.

The cardiac biomarker N-terminal prohormone of brain natriuretic peptide (NT-pro BNP) exhibited a stressed myocardium at screening.

All echocardiographic parameters in Table 2 and the cardiac biomarker depicted in Table 3 as well as the abnormal heart murmur improved continuously during the treatment period and thus clearly demonstrate that a treatment with velagliflozin has a beneficial therapeutic effect on heart failure due to hypertrophic cardiomyopathy (HCM) and/or hypertrophic cardiomyopathy (HCM) in cats.

REFERENCES (1) Atkins C E et al., J Am Vet Med Assoc. 1992, 201(4): 613-618
(2) Freeman L M et al., Cardiol Res. 2017, 8(4): 139-142
(3) Hoenig M et al., J Vet Pharmacol Therapeutics 2018, 41(2): 266-273
(4) Little C J L et al., J Small Anim Prac 2008, 49(1): 17-25
(5) Matsumura K et al, Cardiovascular Ultrasound 2019, 17(1): 26
(6) McMurray J J V et al., Eur. J. Heart Fail. 2019; 21: 665-675
(7) Payne J R et al., J Vet Intern Med. 2013, 27(6): 1427-1436
(8) Payne J R et al., J Vet Cardiol. 2015, 17(Supp 11): S244-S257
(9) Rush J E et al., J Am Vet Med Assoc. 2002, 220(2): 202-207
(10) Santos-Gallego C G et al., J American College Cardiol 2019, 73(15): 1931-1944
(11) Silva Custodio Jr J et al., Heart Failure Reviews 2018, 23(3): 409-418
(12) US 2011/098240
(13) US 2015/164856
(14) US 2016/000816
(15) US 2017/266152
(16) US 2019/076395
(17) WO 2011/153953

The invention claimed is:

1. A method of treatment of one or more cardiac diseases in a feline animal comprising administering to the feline animal one or more SGLT-2 inhibitors or pharmaceutically acceptable forms thereof to treat one or more cardiac diseases, wherein the one or more cardiac diseases comprises one or more of hypertrophic cardiomyopathy (HCM) and heart failure due to hypertrophic cardiomyopathy (HCM) in the feline animal, and the one or more SGLT-2 inhibitors or pharmaceutically acceptable forms thereof comprises Velagliflozin administered to the feline animal at a dose of 0.01 mg/kg bodyweight to 10 mg/kg bodyweight and is represented by the following formula:

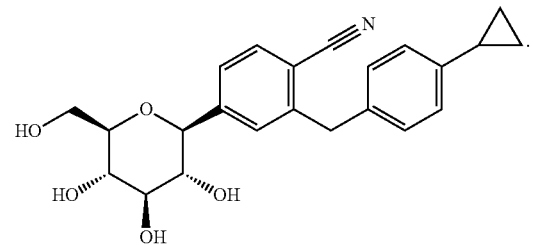 [SMILES: N#Cc1ccc([C@@H]2O[C@H](CO)[C@@H](O)[C@H](O)[C@H]2O)cc1Cc1ccc(C2CC2)cc1]

2. The method of claim 1, wherein the one or more cardiac diseases is further selected from the group consisting of heart failure due to restrictive cardiomyopathy (RCM), heart failure due to dilated cardiomyopathy (DCM), heart failure due to unclassified cardiomyopathy (UCM), and heart failure due to arrythmogenic right ventricular cardiomyopathy (ARVC), hypertrophic cardiomyopathy (HCM), restrictive cardiomyopathy (RCM), dilated cardiomyopathy (DCM), unclassified cardiomyopathy (UCM), and arrythmogenic right ventricular cardiomyopathy (ARVC).

3. The method of claim 1, wherein Velagliflozin is administered to the feline animal at a dose of 0.1 mg/kg bodyweight to 1 mg/kg bodyweight.

4. A method of treatment of one or more cardiac diseases in a feline animal, the method comprising administering to the feline animal a single SGLT-2 inhibitor or a pharmaceutically acceptable form thereof to treat one or more of hypertrophic cardiomyopathy (HCM) and heart failure due to hypertrophic cardiomyopathy (HCM) in the feline animal, wherein the single SGLT-2 inhibitor consists of Velagliflozin represented by the following formula:

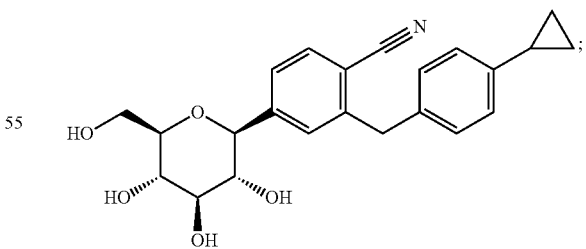

and Velagliflozin is administered to the feline animal at a dose of 0.01 mg/kg bodyweight to 10 mg/kg bodyweight.

5. The method of claim 4, wherein Velagliflozin is administered to the feline animal at a dose of no greater than 2 mg/kg bodyweight.

6. The method of claim 4, wherein Velagliflozin is administered to the feline animal at a dose of 0.1 mg/kg bodyweight to 1 mg/kg bodyweight.

7. The method of claim 4, wherein the feline animal is a non-diabetic cat in need of such treatment.

8. The method of claim 4, wherein Velagliflozin is administered to the feline animal orally, parenterally, intravenously, subcutaneously or intramuscularly.

9. The method of claim 4, wherein Velagliflozin is administered to the feline animal orally.

10. The method of claim 4, wherein the pharmaceutically acceptable form of Velagliflozin is a crystalline complex between Velagliflozin and one or more amino acids.

11. The method of claim 10, wherein the one or more amino acids comprises proline or L-proline.

12. The method of claim 4, wherein Velagliflozin or pharmaceutically acceptable form thereof is administered to the feline animal only once per day or twice per day.

13. The method of claim 4, wherein the therapeutic effect is characterized by one or more of the following clinical and/or biochemical parameters:
improved cardiometabolic efficiency, characterized by an increased ratio of cardiac output/metabolic substrate consumed and/or characterized by an increased ratio of cardiac output/oxygen consumed;
increase of the production of ketone bodies in the liver, characterized by increased plasma levels of 3-hydroxybutyric acid and/or the corresponding acylcarnitines i.e. hydroxybutyrylcarnitine and increased plasma levels of one or more of the branched-chain amino acids valine, leucine and/or isoleucine;
improved cardiac function by achieved reduced pre- and/or afterload, improved arterial wall structure function;
delayed onset of different phenotypes of cardiomyopathies, wherein the delayed onset is at least by 1, 2, 3, 4, 5, 6, 7, 8, 9, 10, 11, 12, 13, 14, 15 or more months, or even stopped progression of different phenotypes of cardiomyopathies;
longer time of survival, at least by 1, 2, 3, 4, 5, 6, 7, 8, 9, 10, 11, 12, 13, 14, 15 or more months, and/or delay of next episode of heart failure, at least by 1, 2, 3, 4, 5, 6, 7, 8, 9, 10, 11, 12, 13, 14, 15 or more months, and/or lower level of cardiac mortality and/or morbidity; and higher quality of life.

14. The method of claim 4, wherein Velagliflozin or pharmaceutically acceptable form thereof is administered to the feline animal before, after or concomitantly with administering one or more other active pharmaceutical ingredients.

15. The method of claim 14, wherein the one or more other active pharmaceutical ingredients is selected from the group consisting of diuretics, beta-blockers, calcium-channel blockers, ACE inhibitors, angiotensin receptor blockers, antiarrhythmic agents, platelet agglutination inhibitors, nonsteroidal anti-inflammatory drugs (NSAIDS), anticoagulants, calcium-channel sensitizers and/or positive inotropes, and combinations thereof.

16. The method of claim 15, wherein:
one or more of the diuretics is selected from the group consisting of furosemide, torasemide, and spironolactone;
one or more of the beta-blockers is selected from the group consisting of atenolol and propranolol;
one or more of the calcium-channel blockers is selected from the group consisting of amlodipine and diltiazem;
one or more of the ACE inhibitors is selected from the group consisting of benazepril, ramipril and enalapril;
one or more of the angiotensin receptors blockers comprises telmisartan;
one or more of the antiarrhythmic agents comprises digitalis alkaloids;
one or more of the platelet agglutination inhibitors comprises clopidogrel;
one or more of the nonsteroidal anti-inflammatory drugs (NSAIDs) comprises aspirin;
one or more of the anticoagulants is selected from the group consisting of Coumarins (vitamin K antagonists), (low molecular weight) heparin, synthetic pentasaccharide inhibitors of factor Xa, direct factor Xa inhibitors and direct thrombin inhibitors; and
one or more of the calcium-channel sensitizers and/or positive inotropes comprises pimobendan.

17. The method of claim 4, wherein the administering Velagliflozin to the feline animal further comprises treating one or more further cardiac diseases selected from the group consisting of heart failure due to one or more cardiomyopathies, heart failure due to restrictive cardiomyopathy (RCM), heart failure due to dilated cardiomyopathy (DCM), heart failure due to unclassified cardiomyopathy (UCM), heart failure due to arrythmogenic right ventricular cardiomyopathy (ARVC), cardiomyopathy, dilated cardiomyopathy (DCM), unclassified cardiomyopathy (UCM), and arrythmogenic right ventricular cardiomyopathy (ARVC).

* * * * *